United States Patent [19]
Stone

[11] Patent Number: 5,912,180
[45] Date of Patent: *Jun. 15, 1999

[54] PROCESS AND APPARATUS FOR TESTING FOR SUBSTANCES IN LIQUIDS

[75] Inventor: Marcia J. Stone, Wellesley, Mass.

[73] Assignee: HybriVet Systems, Inc., Natick, Mass.

[ * ] Notice: This patent is subject to a terminal disclaimer.

[21] Appl. No.: 08/781,580

[22] Filed: Jan. 9, 1997

Related U.S. Application Data

[63] Continuation of application No. 08/441,035, May 15, 1995, abandoned, which is a continuation-in-part of application No. PCT/US94/09215, Aug. 15, 1994, and application No. 08/105,842, Aug. 13, 1993, Pat. No. 5,416,028.

[51] Int. Cl.$^6$ ....................... H01L 21/302; H01L 21/304; H01L 21/306; H01L 21/76
[52] U.S. Cl. ................................. 436/77; 436/76; 436/73; 436/80; 436/81; 436/84; 436/164; 436/174; 436/175; 436/177; 436/178
[58] Field of Search .................................. 436/77, 76, 73, 436/80, 81, 84, 164, 174, 175, 177, 178

[56] References Cited

U.S. PATENT DOCUMENTS

| | | |
|---|---|---|
| 4,790,960 | 12/1988 | Heckmann et al. . |
| 4,986,921 | 1/1991 | Yates et al. . |
| 5,416,028 | 5/1995 | Stone . |

FOREIGN PATENT DOCUMENTS

| | | |
|---|---|---|
| 1170345 | 7/1985 | U.S.S.R. . |

OTHER PUBLICATIONS

Preer et al *Environmental Pollution* (Series B) 12 (1986) 1–13.

Tisue et al *Analytical Chemistry* (1985) 57 pp. 82–87.

Lejla et al *Veterinaria* (Sarajevo) 33(3) 1984 pp. 389–392 (Abstract only).

*Primary Examiner*—Paula K. Hutzell
*Assistant Examiner*—Heather A. Bakalya

[57] ABSTRACT

A method for detecting a substance in a liquid sample involves precipitating a substance from the liquid sample and filtering it from the liquid sample. The precipitate is then tested for the substance of interest by contacting the precipitate with a dye that forms a visible reaction when exposed to the substance. A releasing agent may be used after filtering the precipitate and prior to testing the precipitate with a dye. In another embodiment, the sample is filtered without the prior use of a precipitating agent.

12 Claims, 14 Drawing Sheets

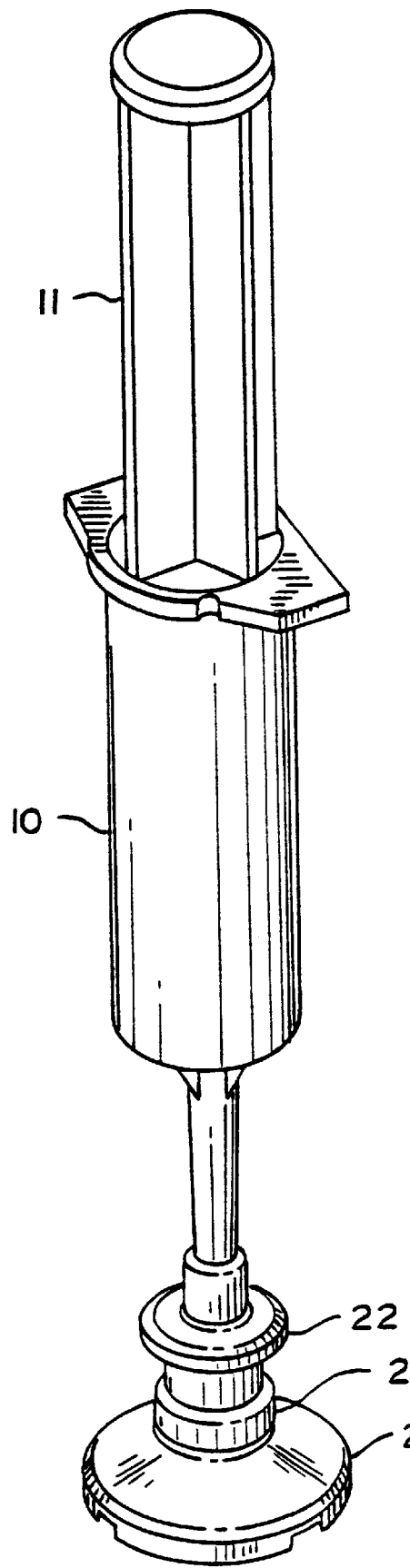
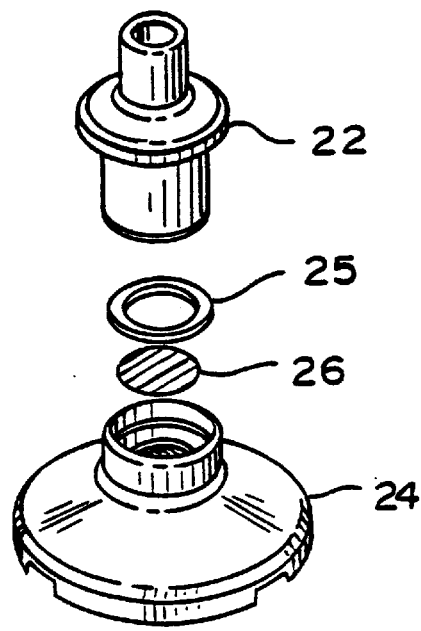
FIG. 2b
FIG. 2a

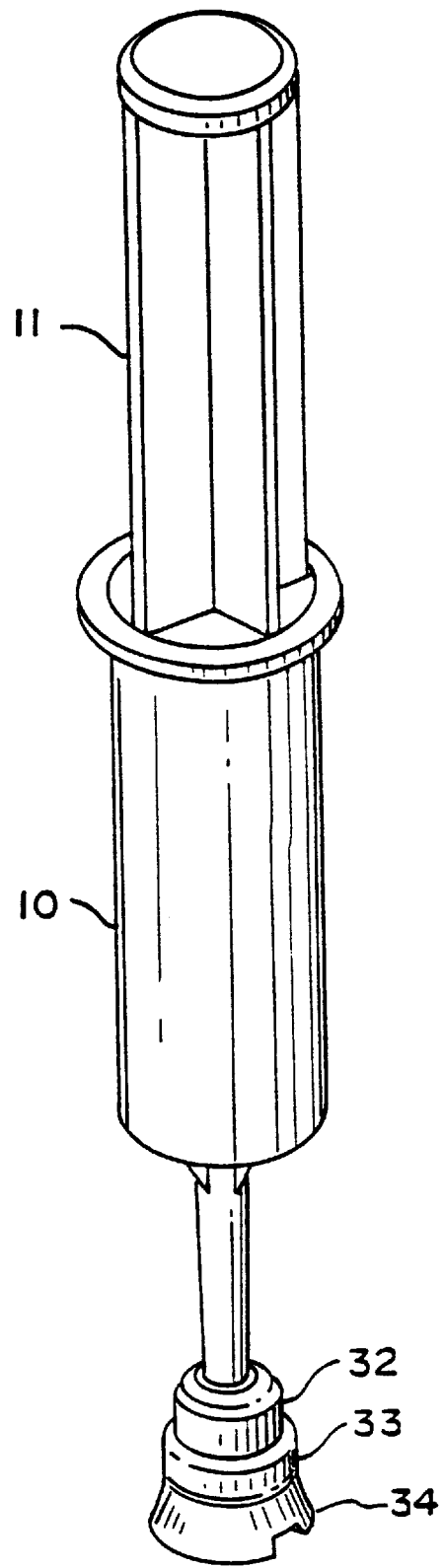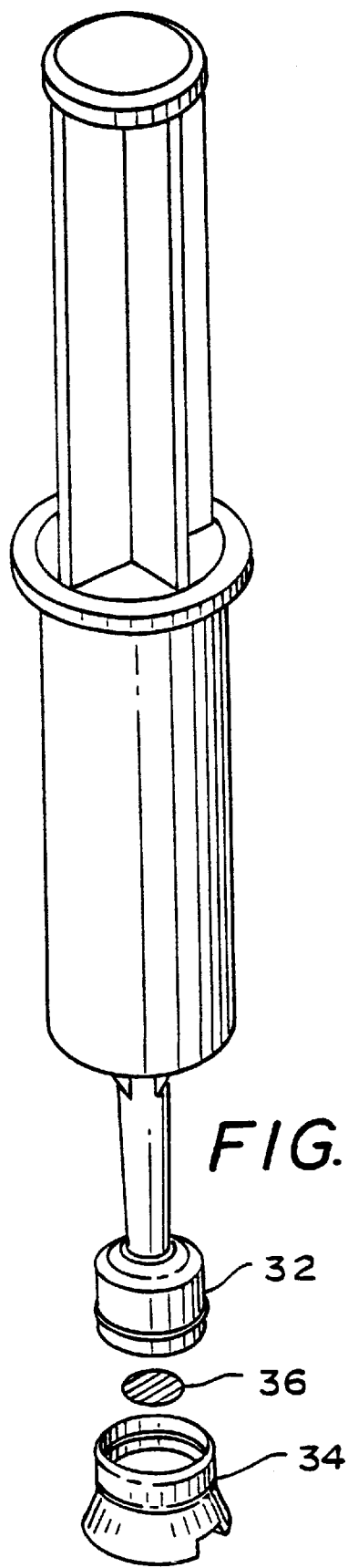
FIG. 3a
FIG. 3b

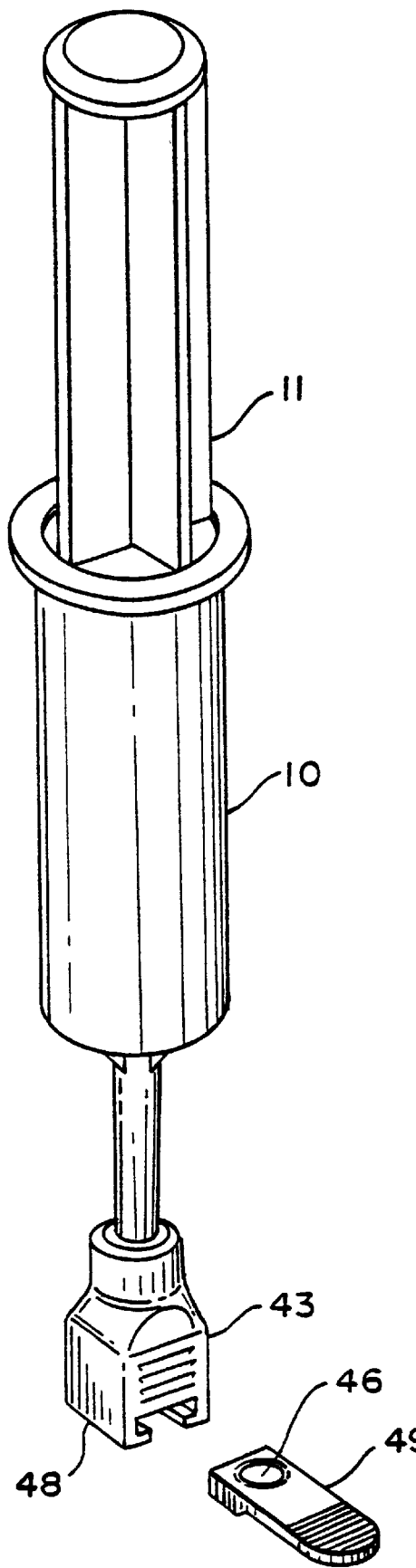
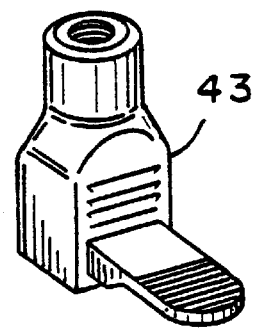
FIG. 4b
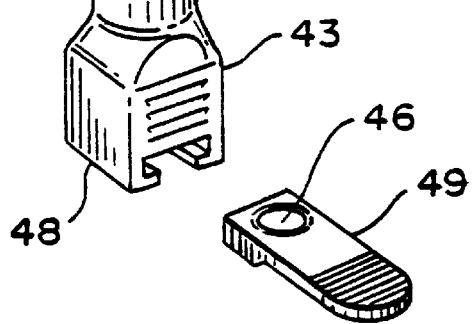
FIG. 4a

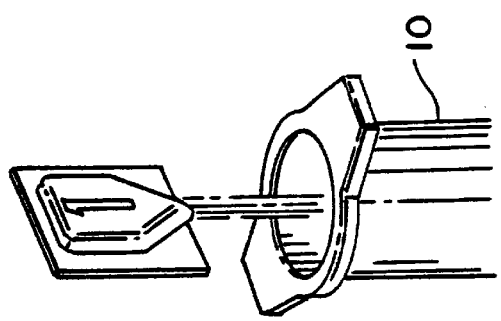
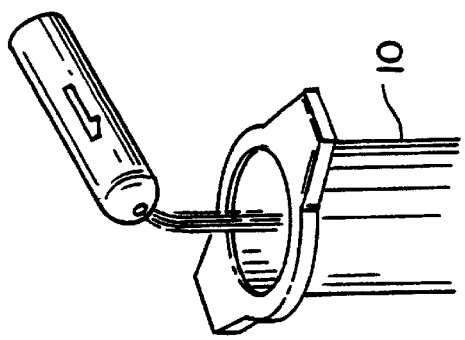
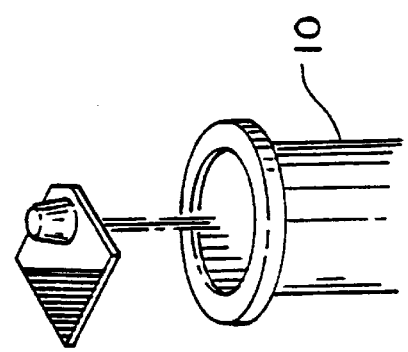
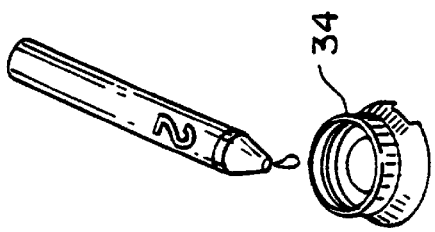
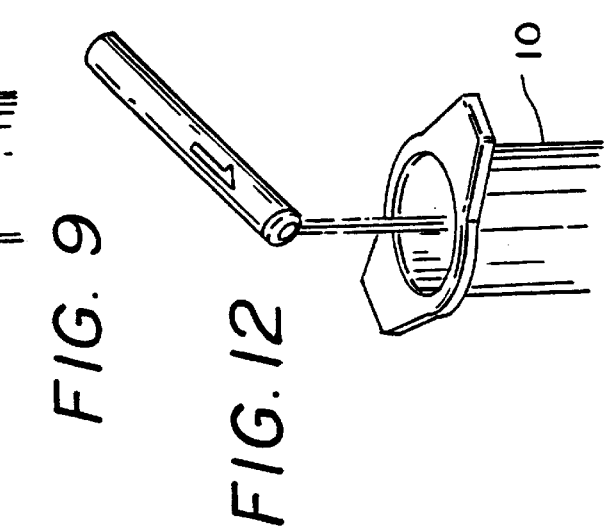

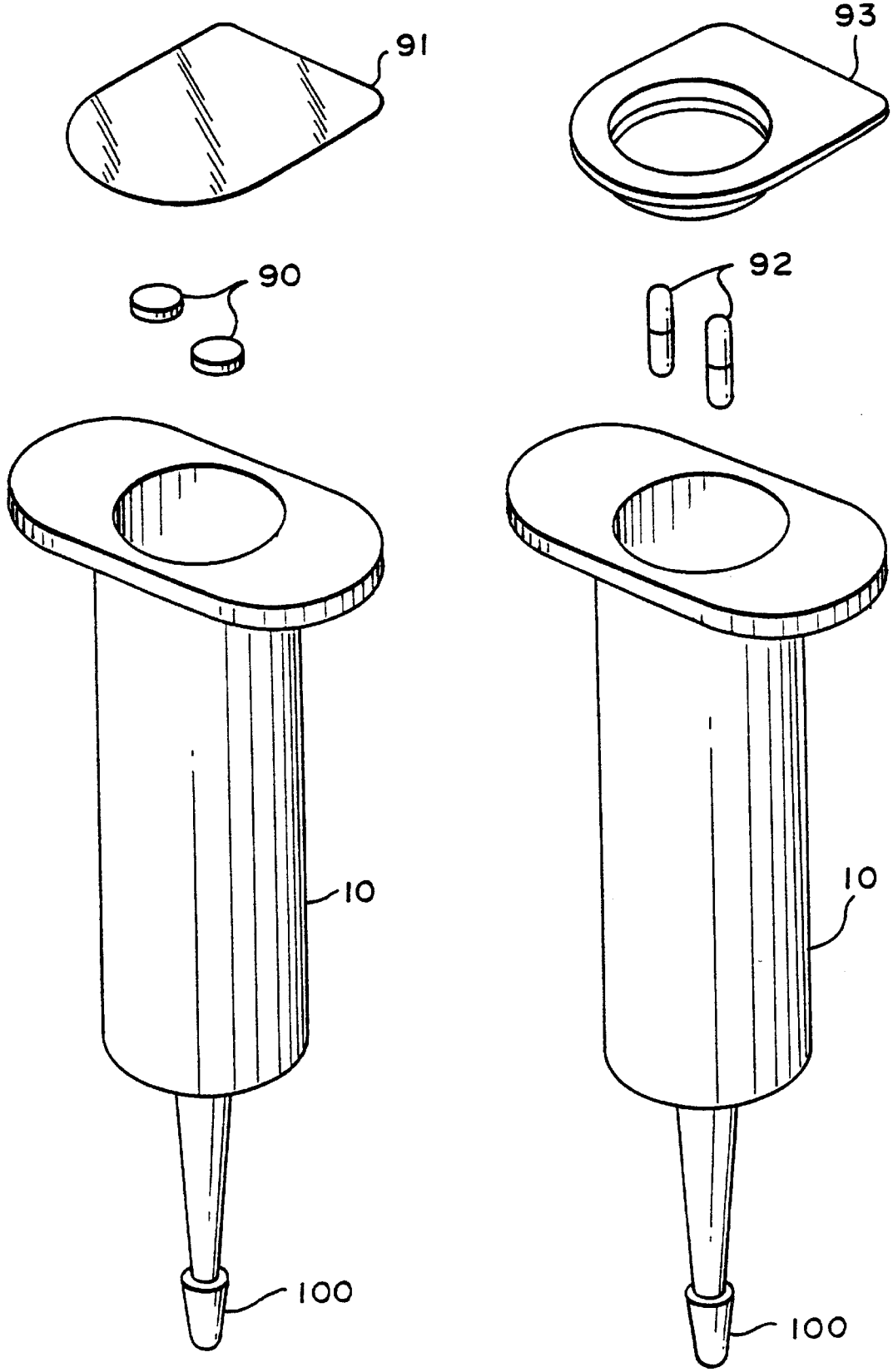

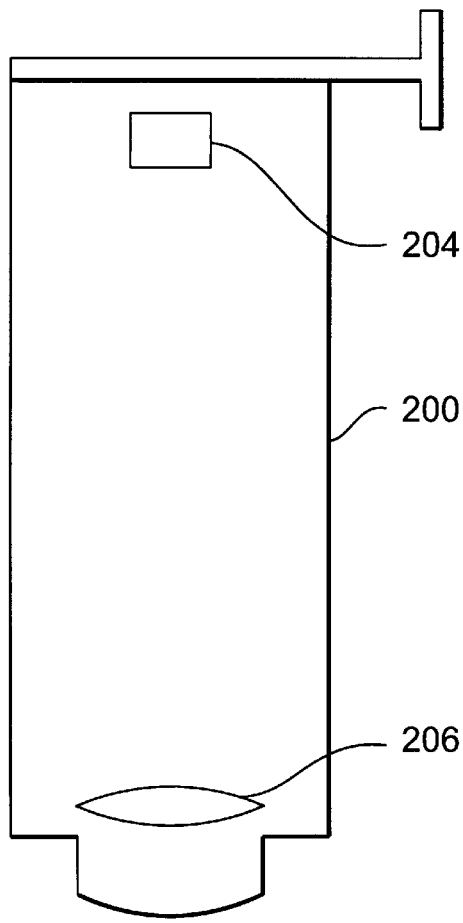
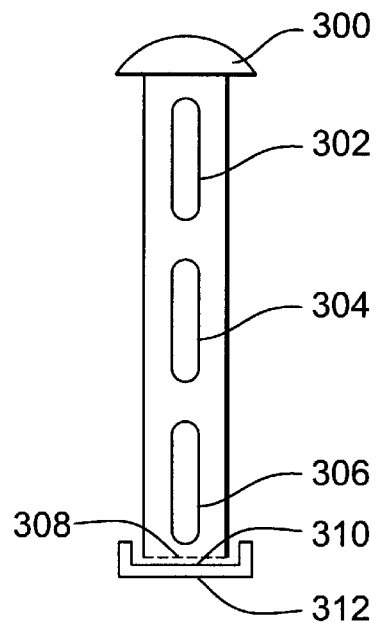
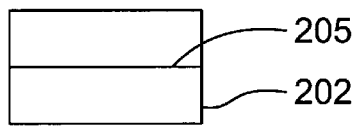
*FIG. 19*
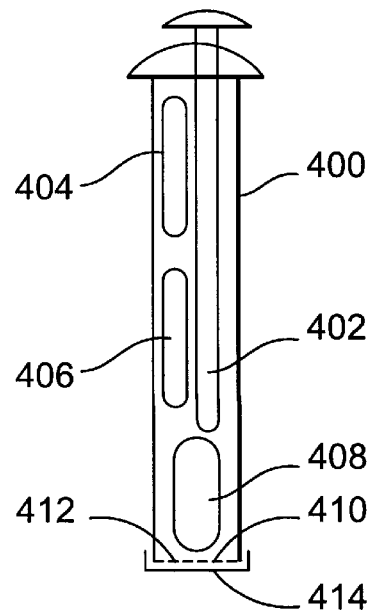
*FIG. 20*
*FIG. 21*

PROCESS AND APPARATUS FOR TESTING FOR SUBSTANCES IN LIQUIDS

CROSS-REFERENCE TO RELATED APPLICATIONS

This application is a continuation of application Ser. No. 08/441,035, filed May 15, 1995 (now abandoned), which is a continuation-in-part of PCT International Application No. PCT/US94/09215, filed on Aug. 15, 1994, and which designated the United States, and a continuation-in-part of Ser. No. 08/105,842 (U.S. Pat. No. 5,416,028), filed Aug. 13, 1993.

BACKGROUND OF THE INVENTION

1. Field of the Invention

This invention relates to a method and apparatus for detecting contaminants, and in particular, heavy metal contaminants in a liquid. More specifically, the invention relates to removing a substance from a liquid and calorimetrically detecting the substance.

2. Background of the Invention

Contamination of the environment has been increasing steadily for years as the use of metals, chemicals, pesticides, and bacterial organisms has increased. Even though the toxicity of various metals has been known for centuries, it is only recently that there has been a serious increase in interest in minimizing human exposure to such metals. Current public awareness of such pollutants and their associated hazards has created a consumer demand for products that are capable of determining the presence of unwanted and potentially dangerous materials.

Some of the more toxic metals include lead, cadmium, mercury, barium, chromium and beryllium. Lead, in particular, has been subject to much attention due to its presence in articles or paints commonly found in the home. See, for example, U.K. Patent Application No. 2 025 047 A; "A Simplified Method for Detection of Lead Contamination of Soil" by J. Preer and G. Murchison, Jr., *Environmental Pollution* (Series B), vol. 12, pp. 1–13; and "A Spot Test for Detection of Lead in Paint" by J. Sayre and D. Wilson, *J. Pediatrics*, vol. 46, pp. 783–785 (1970).

As some of the prior art publications indicate, there is a recognized need in the industry for a simple test or method for determining the presence of lead. However, as will become apparent from the remaining descriptions of the prior art, prior to the present invention, an effective and simple test for lead or other metals in liquid samples had not been developed.

In a well known prior art method of detecting lead in paint, sodium sulfide ($Na_2S$) is reacted with lead to form lead sulfide (PbS), a black precipitate. The presence of lead is thus confirmed by the appearance of the black precipitate, lead sulfide. This method has several disadvantages: (1) the sodium sulfide is potentially toxic, especially to young children; (2) the black precipitate is difficult to see on dark surfaces; (3) the sodium sulfide releases volatile hydrogen sulfide ($H_2S$), which has a noxious odor; and (4) the reagents react with many cations to form black precipitates and thus tend to give false readings on many surfaces.

Another common analytical reagent is a metal complexing agent, rhodizonic acid. For over forty years, rhodizonic acid and salts thereof have been used as analytical reagents to detect heavy metals, including lead, in both qualitative and quantitative analyses. The methodology for using rhodizonate dye is based on two types of tests:

(1) a quantitative determination of heavy metals in solutions using a spectrophotometer to obtain quantitative information; and (2) qualitative determinations which use filter papers impregnated with the reagent.

In addition, semi-quantitative information can be derived from the use of columns packed with silica gel impregnated with rhodizonate dye. See U.K. Patent Application No. 2 025 047 A.

The Macherey-Nagel Company (Düren, Germany) manufactures a test paper for the determination of lead under the trademark PLUMBTESMO. The PLUMBTESMO strips comprise a heavy filter paper with a reagent impregnated therein. To test for lead in a solution, a strip is dipped into the solution, and observed for a color change that indicates the presence of lead. The PLUMBTESMO strips can also be used to detect lead deposits in motor vehicle tailpipes. However, the PLUMBTESMO strips suffer from several disadvantages. First, the chemicals on the strips rub off on the user's hands and clothes after the reaction takes place, causing contamination of other surfaces and requiring constant clean-up. Second, when attempting to use the strips in solutions, other metals interfere with the reaction, potentially causing false results when testing for lead.

Detection of lead in water is generally accomplished by sending a sample to a testing laboratory where the lead content of the sample is determined by analytical instrumental methods, such as atomic absorption spectroscopy, inductively coupled plasma or anodic stripping voltammetry. These instrumental methods are expensive and require sophisticated users.

For example, one method advanced for detecting trace metals in liquid samples involves preparation of a liquid sample, oxidation of organic matter in the sample by boiling with potassium persulfate, treatment of the sample with ammonium pyrrolidinecarbodithioate, filtering the sample and then analyzing the sample by x-ray spectrometry. This process, described in Tisue et. al., "Preconcentration of Submicrogram Amount of Metals from Natural Waters for X-ray Energy Spectrometric Determination Using Pyrrolidinecarbodithioic Acid", *Anal. Chem.*, 57:82–87 (1985), is inaccessible to the average person since the particular equipment required is not available. Moreover, the x-ray spectrometry is extremely sensitive to contaminant metals which may be introduced by the oxidizing agent. In this case, ultra-pure chemicals must be manufactured in order to avoid contamination. Finally, the test described in Tisue et. al. requires heating the persulfate in order to oxidize the organic matter in the sample, which is disadvantageous in a home use test.

A different method of detecting trace metals in liquid is described in Lo et. al., "Solvent Extraction of Dithiocarbamate Complexes and Back-Extraction with Mercury(II) for Determination of Trace Metals in Seawater by Atomic Absorption Spectrometry", *Anal. Chem.*, 54:2536–2539 (1982). This procedure involves the extraction of metal-dithiocarbamate complexes into chloroform followed by back-extraction with a dilute mercury solution. This method involves extremely hazardous chemicals and requires monitoring and controlling the Ph levels of each solution utilized. Moreover, this method is not available to the average person due to the complexity of the process, the chemicals used and the equipment needed to conduct the x-ray spectrometry.

Colorimetric methods for the specific determination of a substance such as lead in a liquid such as water have heretofore been unavailable because of the sensitivity required. "A Simple Direct Estimation of Ultramicroquantities of Lead in Drinking Water Using Sodium Rhodizonate" by E. Jungreis and M. Nechama, *Microchemical Journal*, vol. 34, pp. 219–221 (1986) describes a test which can only detect lead in amounts above about fifty parts per billion. This test involves a number of steps, including preparation of a reagent test strip, heating a solution to dryness and development of the test spots. The reagents used include nitric acid and hydrochloric acid, which are not available or widely used by the average person.

Thus, it should be clear that the lead tests known prior to the present invention are not entirely satisfactory. Therefore, there is a need in the art for a test or method for determining the presence of toxic metals, such as lead. Furthermore, there is a need in the art for a simple, easy-to-use test for determining the presence of metals in a liquid sample.

OBJECTS AND SUMMARY

Accordingly, an object of the present invention is to provide a method for testing liquid samples for the presence of metals.

Another object of the present invention is to provide a calorimetric method for the detection of heavy metal contaminants in a liquid sample.

Another object of the present invention is to provide an easy to use apparatus for testing for metals in liquid samples which does not use hazardous chemicals.

According to the present invention, a method for detecting a substance in a liquid sample is provided comprising mixing the liquid sample with a first reagent that causes the substance to precipitate, filtering the precipitate from the liquid sample, and testing the precipitate for the substance by contacting the precipitate with a second reagent that forms a visible reaction when exposed to the substance.

In another embodiment of the present invention, a method is provided comprising pretreating the liquid sample with a first oxidizing agent, mixing the pretreated liquid sample with a first reagent that causes the substance to precipitate, filtering the precipitate from the liquid sample, and testing the precipitate for the substance by contacting the precipitate with a second reagent that forms a visible reaction when exposed to the substance.

In yet another embodiment of the present invention, a method is provided comprising forcing a liquid sample through a fine mesh filter, causing a substance in the liquid sample to adhere to the filter, and testing the filter for the substance by contacting the filter with a reagent that forms a visible reaction when exposed to the substance.

In another embodiment, an apparatus for detecting a substance in a liquid sample is provided comprising a container for holding the sample, a filter holder having a top portion and a detachable bottom portion connected to the container, a filter supported in the detachable bottom portion of the filter holder, and a means for pushing the sample through the filter which fits into the container.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 2*a* is an embodiment of a test apparatus according to the present invention. FIG. 2*b* is an exploded view of the filter arrangement in the test apparatus of FIG. 2*a*.

FIG. 3*a* is an embodiment of a test apparatus according to the present invention. FIG. 3*b* is an exploded view of the filter arrangement in the test apparatus of FIG. 3*a*.

FIG. 4*a* is an exploded view of an embodiment of a test apparatus according to the present invention. FIG. 4*b* is a view of the filter arrangement in the test apparatus of FIG. 4*a*.

FIGS. 9–14 are embodiments of containers used to provide chemical reagents in the test apparatus of the present invention.

FIGS. 15–21 illustrate embodiments of storing chemicals directly in the container for the test apparatus of the present invention.

DETAILED DESCRIPTION OF THE PREFERRED EMBODIMENTS

Figure 1A:
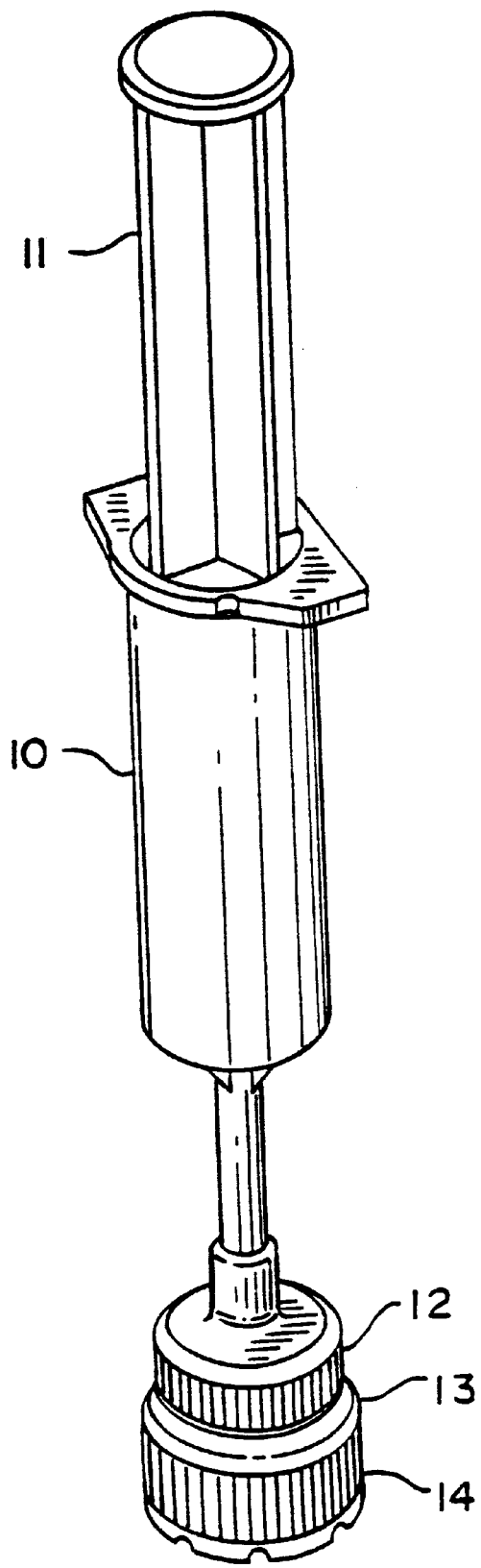
FIG. 1*a* is an embodiment of a test apparatus according to the present invention.

The subject matter of PCT International Application No. PCT/US94/09215, filed on Aug. 15, 1994, and which designated the United States, the subject matter of U.S. patent application, Ser. No. 08/105,842, filed Aug. 13, 1993 and Ser. No. 08/325,149, filed Oct. 20, 1994, and the subject matter of U.S. Pat. Nos. 5,039,618; 5,278,075; 5,330,917; and 5,364,792 are hereby incorporated herein by reference. In addition, two copending applications of the same title and inventor are filed concurrently herewith. The subject matter of the copending applications is also incorporated herein by reference.

The method of the present invention allows for the quick and safe detection of metals in liquid samples. Previously known methods for detection of metals in liquids have required hazardous chemicals, numerous steps and/or expensive, complicated equipment. Some of the previous methods used to detect metals in liquid samples, such as heating a solution to dryness or chelating a metal with traditional chelators, are unsatisfactory because the metal is insufficiently concentrated to be detected by calorimetric means. Other methods, such as precipitation methods, provide complexes with the metal so stable that the metal is not available for detection by colorimetric means. It has now surprisingly been found that by precipitating the metal with a precipitating agent and then treating the precipitate with a metal releasing agent, the metal can be concentrated into a small amount of precipitate and then made available to react with dyes to provide a detectable color change indicating the presence of a particular metal.

The method and apparatus of the present invention may be used to detect a variety of substances, depending on the reagent or dye used to provide the detectable color change. A number of metals, including $Au^{3+}$, $Pd^{2+}$, $Hg^{2+}$, $Ag^+$, $Po^{4+}$, $Bi^{3+}$, $Cu^{2+}$, $Ni^{2+}$, $Pb^{2+}$, $Cd^{2+}$, $As^{3+}$, $Zn^{2+}$, $Fe^{2+}$, $Co^{2+}$, $Tl^+$ and $Mn^{2+}$, may be detected according to the teachings of the present invention. In particular, the test apparatus may be used to determine the presence of lead, cadmium, bismuth, mercury, cobalt, arsenic, tin, antimony, iron, aluminum, selenium or copper. The metals most likely to be detected with the present invention will be lead, bismuth, mercury, arsenic, and copper.

Table I also identifies a number of potential substances that may be detected using the teachings herein. Appropriate reagents are also set forth in Table I. Because of their teachings of reactions that are suitable for detecting substances, the subject matter of U.S. Pat. Nos. 5,039,618; 5,278,075; 5,330,917; and 5,364,792 and pending application Ser. No. 08/325,149 filed Oct. 20, 1994 are incorporated herein in their entirety by reference. Accordingly, the present invention includes testing for any of the substances set forth in the above-listed patents using the techniques and apparatuses disclosed herein.

The method of the present invention provides a means of determining whether or not a particular substance, such as a metal, is in a liquid sample. Preferably, the method of the invention will be carried out in aqueous solutions. The invention will find a variety of uses, particularly in the testing of water, including the testing of rivers and lakes and, preferably, drinking water.

TABLE I

| Metal | Dye (Reagent which Reacts with Metal) | Activating Solution | Color |
|---|---|---|---|
| Bi | Cinchonine - KI (1%) | Dilute acid | Orange Red |
| Hg | 1) Diphenylcarbazide (1% in alcohol) | 0.2M $HNO_3$ | Violet |
|  | 2) Cobalt (II) thiocyanate test | Cobalt (II) acetate | Deep blue |
| Sb | 1) Rhodamine B (Tetraethylrhodamine) | $Sb^{+5}$ nitrite | Blue |
|  | 2) Phosphomolybdic acid | $Sb^{+3}$ | Blue |
| Fe | 1) 2,2'-bipyridine or 1,1' phenanthroline | Thioglycolic acid buffer | Red |
|  | 2) 3-(2-pyridyl)-5,6-bis(4-phenyl-sulfonic acid) | 1,2,4-triazine, sodium salt | Purple |
| Al | 1) Aurin tricarboxylic acid | NaOH | Red |
|  | 2) Quinolizarin | Ammonia, then glacial HOAC | Red |
| Se | Pyrrole reagent | 0.5M iron (III) chloride; $H_3PO_4$ | Green-Blue |
| Cu | 1) Quinolyl reagent (0.2 g/l in amyl alcohol) | 20 g Na acetate 10 g K Na tartrate 3 g hydroxyl-ammonium Cl (all in 100 ml $H_2O$) | Red |
|  | 2) Dithiooxamide (1% in acetone) (Rubeanic acid) |  | Dark-Green |
| Co | Rubeanic acid | Ammonia/alkali tartrates | Brown |
| As | Magnesium nitrate/ammonium chloride | Silver nitrate | Red |
| Sn | Sodium sulfide | dilute acid | Brown ($Sn^{+2}$)/ Yellow ($Sn^{+4}$) |

According to the present method, a pretreatment step, using a first oxidizing agent may be utilized prior to precipitating the substance of interest from the liquid sample. The pretreatment (preoxidation) step preferably is used when one or more sequestering agents are present in the liquid sample which will prevent the metal or other substance from being available for precipitation, or otherwise being detectable. The preoxidation step breaks apart the complexes that metals form with organic substances in some aqueous samples, such as sea water. These organic substances may be "humic" from humic acid or "fulvic" found in the water which form complexes with metals, such as lead, in water samples. Thus, this pretreatment step may be needed to break up the complexes and allow for the complete precipitation or detection of a metal as it is found in liquid samples. However, the preoxidation step is not necessary in fairly clean liquid samples or where a sufficient amount of metal can be precipitated or detected from the solution without the preoxidation step to allow detection of the metal by calorimetric means.

The oxidizing agent can be any of a number of oxidizing compounds known to those of skill in the art. Preferably, the oxidizing agent comprises a bleach compound, such as sodium hypochlorite, sodium chlorite, calcium hypochlorite, peroxides, perchlorates, and hypochlorous acid, among others. In the preferred embodiment, CLOROX®, which is a source of sodium hypochlorite, is used as the oxidizing agent in the pretreatment step. Generally, the bleach contains a concentration of bleaching agent of about 3 to about 15%. In a preferred embodiment, the bleach will contain a concentration of about 5 to about 7%. When used in the method of the present invention, about 5.0 to about 10.0 ml of bleach is used per 100 ml of liquid sample.

After the bleach is added to the liquid sample, the sample generally will be allowed to sit at room temperature for about one hour to about 12 hours. Typically, the sample will sit for about two hours.

After the pretreatment step or initially, if no pretreatment step is used, a precipitating reagent is added to the liquid sample in order to precipitate out the metal to be detected. This reagent may be added simultaneously with the first oxidizing agent, but it is preferred that the reagent be added either immediately after the oxidizing agent or after an incubation period. This reagent can be any agent which can precipitate a metal out of solution, such as a chelator or other precipitating agent. In a preferred embodiment, this agent is oxidizable.

In a preferred embodiment intended to test for lead, the precipitating reagent is borate. For convenience, the borate can be combined with an inert filler that can be tableted, such as salt, and is incorporated into a tablet which can be added to the liquid sample. For 100 ml of liquid sample, a tablet containing 0 to 400 mg of borate is recommended, preferably 40 to 160 mg, and most preferably about 80 mg of borate.

Sodium borate, or any soluble form of borate may be used as the precipitating agent.

It has been found that when APDC was used as the precipitating reagent for a lead test, it is difficult to detect the lead in the precipitate unless a releasing agent is first used to release the lead from the precipitate complex. In those tests, an oxidizing or releasing agent is applied to the precipitate, which frees up the lead, thus making it easy to detect. See U.S. Pat. No. 5,416,028.

An advantage of using borate as the precipitating reagent is that when the lead precipitates, the bonds of the precipitate complex are such that the lead can be detected in the precipitate without having to use a releasing or oxidizing agent prior to the detection step. Presumably, the bonds in the precipitate complex formed when using borate as a precipitating agent are not as strong as those formed when APDC is used as a precipitating agent.

Those of ordinary skill in the art will appreciate that other metals or substances may be precipitated with borate. Accordingly, the teachings of the present invention include testing for such other metals and substances as well. The following Table II identifies several metals that also precipitate with borate and thus may also be tested according to the principles of the present invention. Table II also identifies a preferred reagent for testing the precipitate for the substance of interest.

With respect to copper and iron, the reaction of the metal with borate creates a colored precipitate that can be identified without having to use another reagent.

Accordingly, it is not necessary to use an additional reagent to check the precipitate for copper or iron.

TABLE II

| METAL | DETECTION REAGENT | OBSERVATION NO BORATE | OBSERVATION WITH BORATE |
|---|---|---|---|
| Lead ($Pb^{+2}$) | LeadCheck Swab | Pale pink | Pink/red |
| Mercury ($Hg^{+2}$) | MercuryCheck Swab | Pink | Purple |
| Nickel ($Ni^{+1}$) | Dimethylglyoxime | Yellow | Deep pink |
| Chromium ($Cr^{+3}$) | LeadCheck Swab | Clear | Yellow/green |
| Cobalt ($Co^{+2}$) | LeadCheck Swab | Clear | Yellow/brown |
| Tin ($Sn^{+2}$) | Leadcheck Swab | Yellow | Deep blue |
| Copper ($Cu^{+2}$) | None | Little | Deep blue |
| Iron ($Fe^{+3}$) | None | Pale yellow | Pale Yellow |

The precipitating reagent may be mixed with a carrier metal. In addition, any buffer compatible with the solution and precipitating reagent may also be mixed with the precipitating reagent.

The precipitating reagent, buffer and carrier metal will preferably be provided in amounts which result in maximum precipitation of the metal of interest. However, the precipitating reagent is preferably used in excess to ensure proper precipitation, more preferably, in an amount 5 to 25 fold in excess of the amount of metal expected in the sample.

The carrier metal may be any metal which has less affinity for the precipitating agent being used than the metal for which the test is performed. It has been found that in some solutions, the level of metal is so low that the precipitating reagent does not function very well. By adding an additional carrier metal to provide ions in solution, the precipitation step can be performed more effectively. The carrier metal should be provided in amounts that are just enough to aid in the precipitation. The carrier metal may be added at any time prior to or simultaneously with the precipitation step. Carrier metals which may be used include zinc and iron. Preferably, a zinc compound is included in the APDC mixture. In a preferred embodiment, the zinc compound is zinc acetate.

In a preferred embodiment, 0–1.35 mg of zinc acetate is used per 100 ml of liquid sample, more preferably 0.34 to 0.56 mg of zinc acetate is used, and most preferably, 0.45 mg of zinc acetate is used for a 100 ml sample.

Other zinc salts, preferably water soluble, would also work as a carrier. In addition, cobalt, or other metals may function as a carrier, provided that the selected carrier does not interfere with the readout for the substance being detected.

A zinc acetate carrier was used with the metals in Table II to facilitate their detection.

After the metal is precipitated by a precipitating reagent such as borate, the liquid sample is filtered, so that the precipitate will collect on a filter. Any filter which can collect the precipitate may be used. Preferably, the filter will be a glass fiber filter such as Gelman Type A/E glass fiber (pore size: 1 micron), PFG3 filter (millipore 1.2 micron), PFG2 filter (Millipore 1.0 micron) or PFG5 filter (Millipore 0.7 micron). Alternatively, a hydrophilic polysulfone membrane filter may be used.

It has also been discovered that the effects of the filter can be enhanced by placing small glass beads on the filter prior to pushing the sample through the filter. For example, glass beads having a mesh size of 120–200 with a mean pore diameter of 115 Å have been used.

The diameter of the filter should not be too large since the purpose of the precipitation procedure is to concentrate the metal in a small area. The sensitivity of the test may be reduced if the metal is spread out too much on the filter. Generally, the filter should be from about 7 mm to about 17 mm in diameter for a 100 ml sample. Preferably, the filter is from about 10 mm to about 15 mm in diameter. The preferred diameter of the filter is proportional to the amount of sample pushed through the filter.

After the precipitate is filtered, the precipitate is tested to determine the presence of the substance for which the test is being conducted. Preferably, a dye-containing reagent such as those listed in Table I is used to test the precipitate for the metal or substance. For detecting lead, a salt of rhodizonic acid is preferably used. In a preferred embodiment, sodium rhodizonate is used to detect lead in the precipitate.

In a preferred embodiment, the test swabs described in U.S. Pat. Nos. 5,039,618; 5,278,075; 5,330,917; and 5,364,792 and U.S. patent application Ser. No. 08/325,149 are used to detect metals in the precipitate.

The method of the present invention is sensitive enough to detect lead at levels as low as 15 ppb, which is the current EPA hazard limit.

In some applications, particularly when borate is not used as the precipitating agent, a releasing agent may be used on the precipitate prior to testing the precipitate for the concerned substance. Such a step may release the metal or substance from the precipitate complex so that the metal can be more easily calorimetrically detected. The metal releasing agent may be an oxidizing agent, an agent that allows for the displacement of metals, or any other agent known by those of skill in the art. The choice of metal releasing agent will depend on the choice of precipitating reagent. For example, if a chelating agent is used as the precipitating reagent, a metal displacement reaction may effectively provide a release of the metal to be detected. If an oxidizable precipitating agent is used, an oxidizing agent may be used to release the metal for detection.

Generally, the metal releasing agent will be any reagent which releases the metal from the precipitate complex without affecting a further calorimetric detection step. Preferably, the metal releasing agent is an oxidizing agent such as peroxides, chlorates and perchlorates. In one embodiment, the releasing agent is a solution of ethyl acetate and either hydrogen peroxide or urea peroxide.

The metal releasing agent "clears" the filters after filtering the precipitate complexes, releasing the metal for detection. Hydrogen peroxide, in particular, has been found to be effective at releasing lead from an APDC-lead complex so that the lead can be measured or detected by rhodizonate dye or other lead detecting dye. When zinc is used as the carrier metal, the lead precipitate will generally be a colored precipitate which turns white as the filter clears.

The concentration of the hydrogen peroxide or other oxidizing agent should be balanced such that the metal is released from the precipitate complex, but the dye to be used is not oxidized.

Generally, if used, the metal releasing or oxidizing agent will have a concentration of about 1 to about 30%. Preferably, the oxidizing agent will have a concentration of about 3 to about 8%.

A drop of the metal releasing agent is placed on the precipitate and allowed to stand on the precipitate overnight or until the filter clears. In the some embodiments, the releasing agent need only contact the precipitate for 0–5 minutes. After the filter clears, the metal can be detected by any calorimetric or instrumental means to obtain a qualitative or quantitative result.

The apparatus of the present invention can be made in a variety of formats as shown in the figures and described below. Generally, the apparatus will have a container for holding the liquid sample and the chemical additions thereto. The container preferably is fitted with a filter holder which has a top portion and a detachable bottom portion. The bottom portion is fitted with a filter for retaining the precipitate. The container is fitted with a means for pushing the liquid sample through the filter after the precipitate is formed. As shown in the figures, the container for holding the sample is preferably a syringe, but any container may be used which enables the user to mix the necessary chemicals and filter the precipitate. In a preferred embodiment, the container is a syringe or cartridge and the means for pushing the liquid sample through the filter is the syringe or cartridge plunger.

Referring now in detail to the drawings, wherein like reference numerals refer to like elements throughout, in the embodiment of FIG. 1a, syringe 10 is fitted with plunger 11. The liquid sample is placed in syringe 10 and the various chemicals are added to the sample in the syringe. During this step the syringe tip is plugged or capped. Alternatively, the sample may be pretreated and mixed with the precipitating reagent in a container and then the precipitated solution is poured into the syringe 10.

Figure 1B:
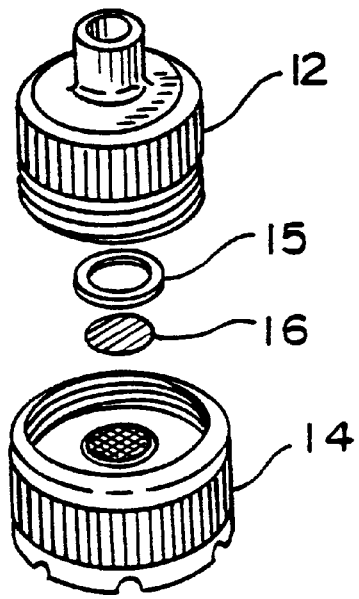
FIG. 1*b* is an exploded view of the filter arrangement in the test apparatus of FIG. 1*a*.

After the precipitation step, filter holder 13 is attached to the syringe and the plunger is used to push the sample through the filter supported in filter holder 13. The filter holder 13 has an upper housing 12 and lower housing 14 which can be taken apart to reveal the filter. As shown in FIG. 1b, the filter holder 13 is comprised of several parts: the upper housing 12, the lower housing 14, the filter retaining ring 15 and the filter 16. The filter holder 13 preferably is custom molded to force fit the tip of a stock syringe. The lower housing 14 unthreads from the upper housing 12 and doubles as a small stand that holds the filter during the clearing and/or testing stages after the precipitate is collected on the filter. The lower housing 14 has small notches on the bottom around the perimeter to allow the liquid to escape as the sample is pushed through the filter.

FIG. 2a illustrates an alternative embodiment of the apparatus of the present invention. Syringe 10 is fitted with plunger 11 and filter holder 23. FIG. 2b shows filter 26 and retaining ring 25 in filter holder 23, which is custom molded to force fit the tip of a stock syringe. Lower housing 24 is unsnapped from upper housing 22 after the precipitation step and doubles as a small stand that houses the filter during the clearing and/or testing stages. As with lower housing 14, housing 24 has small notches on the bottom around the perimeter to allow the water to escape.

FIG. 3a shows a further alternative embodiment of the invention, wherein the filter holder 33 snaps onto a custom made syringe tip 32. The filter 36, shown in FIG. 3b, is glued to the filter base 34, eliminating the need for a retaining ring.

FIGS. 4a and 4b show a further alternative embodiment of the invention, which uses a stock syringe 10, plunger 11 and custom molded filter holder 43. Filter holder 43 has a main housing 48 and a filter slide 49. Filter 46 is glued to the filter slide which holds the filter during the precipitate collection, clearing and/or testing stages. Refill filter slides will preferably be used for additional tests using this embodiment.

Figures 5A, 5B:
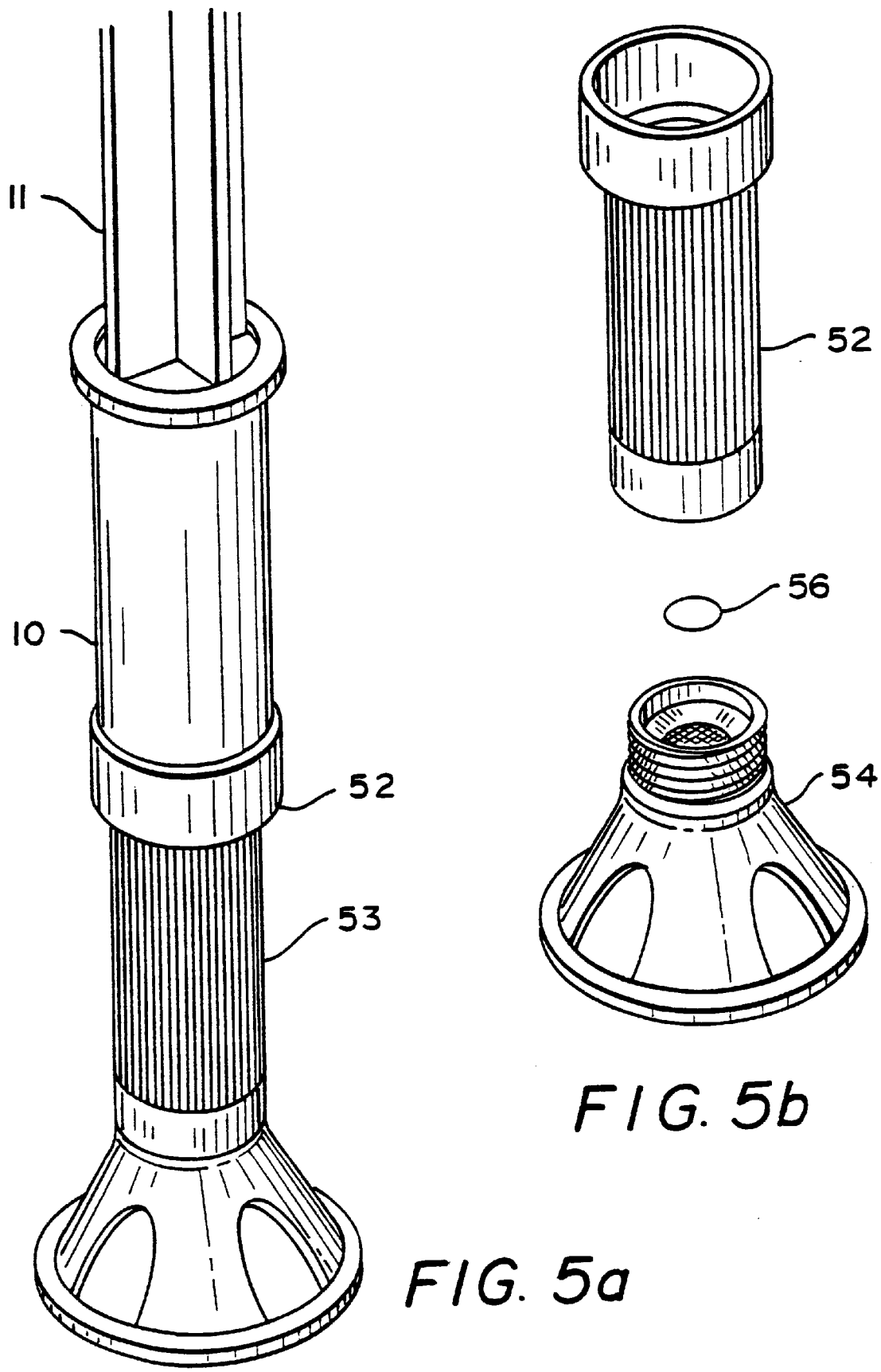
FIG. 5*a* is an embodiment of a test apparatus according to the present invention.
FIG. 5*b* is an exploded view of the filter arrangement in the test apparatus of FIG. 5*a*.

In another alternative embodiment, shown in FIG. 5a, a custom molded filter holder 53 is force fit to the tip of the syringe 10 and comes up under the lower part of the syringe to help support the unit when pressure is applied to plunger 11. Lower filter housing 54, shown in FIG. 5b, unthreads from upper housing 52 and doubles as a small base that holds the filter 56 during the clearing and/or testing stages. The large, stable stand has openings to allow the liquid to escape.

Figure 6A:
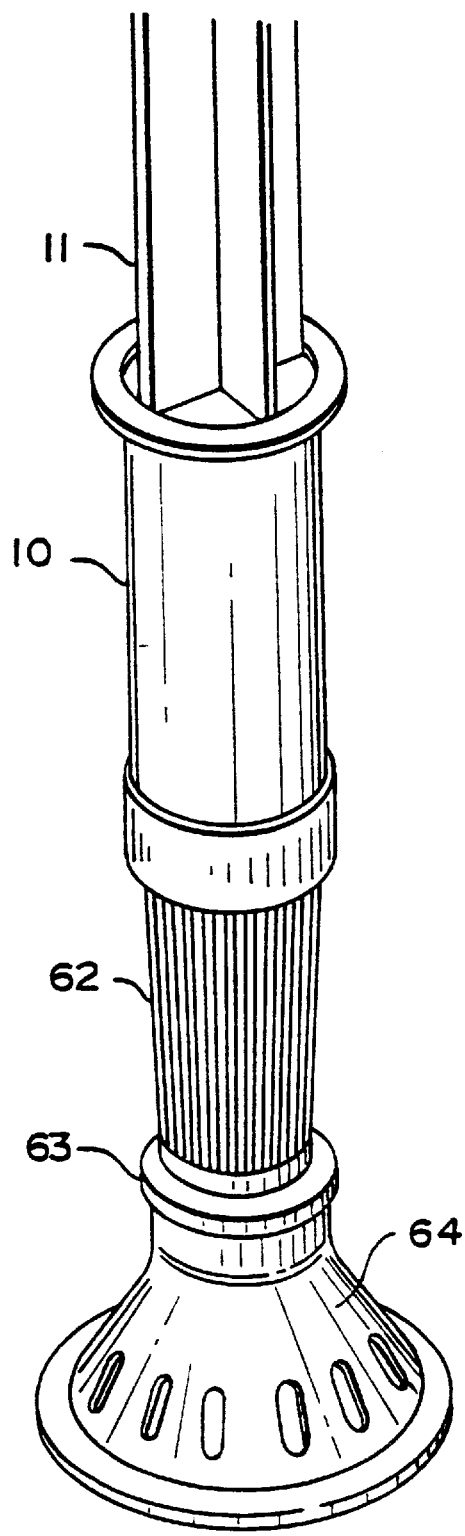
FIG. 6*a* is an embodiment of a test apparatus according to the present invention.
Figure 6B:
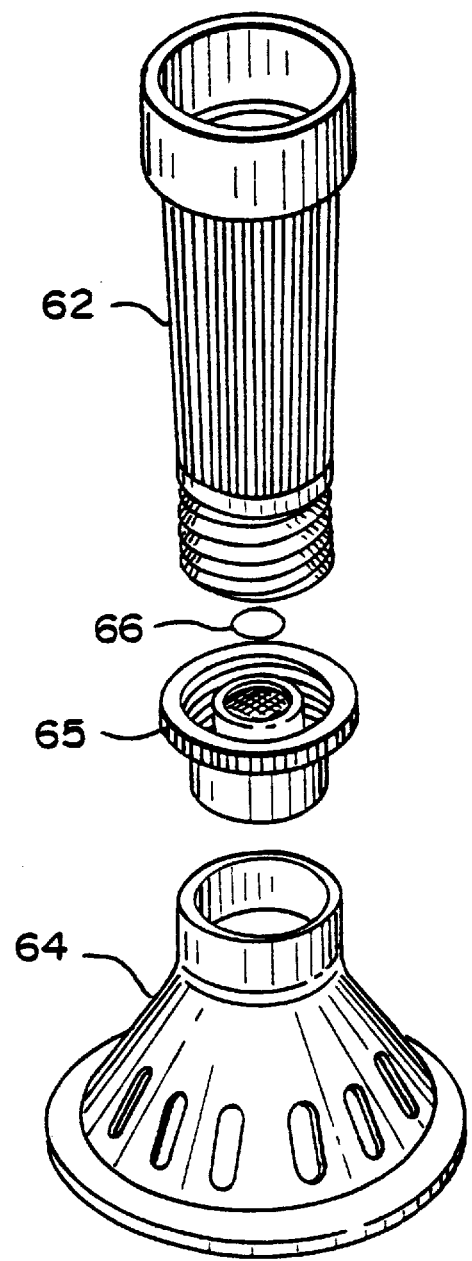
FIG. 6*b* is an exploded view of the filter arrangement in the test apparatus of FIG. 6*a*.

FIGS. 6a and 6b illustrate an alternative embodiment wherein filter holder 63 is force fit to the tip of stock syringe 10 such that it comes up under the lower part of the syringe to help support the unit when pressure is applied to the plunger. Filter holder 63 contains filter 66 and filter carrier 65 supported on lower housing 64.

Figure 7A:
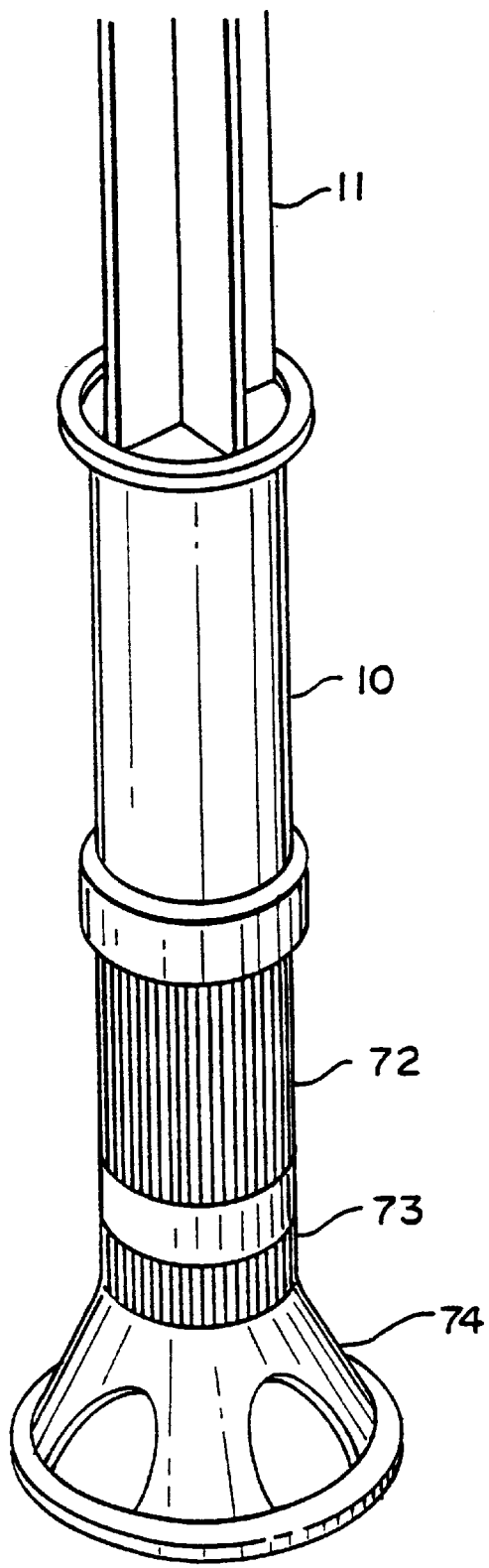
FIG. 7*a* is an embodiment of a test apparatus according to the present invention.
Figure 7B:
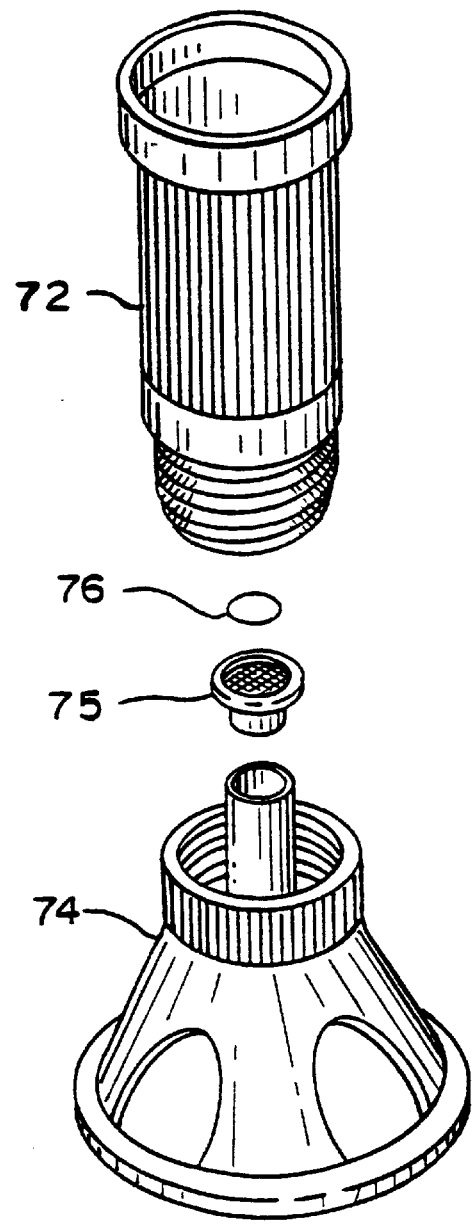
FIG. 7*b* is an exploded view of the filter arrangement in the test apparatus of FIG. 7*a*.

In the preferred embodiment shown in FIGS. 7a and 7b, filter holder 73 is force fit onto syringe 10. Filter holder 73 has an upper housing 72, a lower housing 74, a filter carrier 75 and a filter 76. The filter carrier is positioned with easy access and viewing in mind. Upper housing 72 threads into lower housing 74 to seal filter carrier 75 between the two housings during the filtration and/or metal releasing steps. Filter carrier 75 then unsnaps from lower housing 74 for the clearing and/or testing steps after lower housing 74 is unthreaded from upper housing 72.

The apparatus of the invention is preferably used in a test kit for detecting a substance in a liquid sample. The test kit comprises a container for holding the sample, a filter holder having a top portion and a bottom portion connected to the container, means for introducing a first oxidizing agent and a precipitating reagent into the sample, means for filtering the precipitate connected to the bottom portion of the filter holder, means for forcing the liquid sample containing the precipitate through the means for filtering, means for introducing a second oxidizing agent onto the precipitate, and means for introducing a dye onto the precipitate which forms a visible reaction when exposed to the substance.

The method of the invention may be carried out by use of the test kit. The liquid sample is first placed in the container for holding the sample, after which a pretreating (e.g., oxidizing) agent (if necessary) and then the precipitating reagent, with or without a carrier, are added to the sample. After the precipitation is complete, the means for forcing the liquid sample through the filter is utilized to place the precipitate on the filter. The bottom portion of the filter holder is then disconnected from the top portion and the releasing agent (if necessary) is introduced onto the precipitate. After this step is complete, a dye is introduced onto the precipitate which forms a visible reaction when exposed to the substance of interest.

The means for introducing the pretreating agents, the precipitating reagent, the releasing agent, and the dye into the liquid sample or onto the precipitate may be any means normally used for dispensing chemicals, such as pipettes, medicine droppers and beakers, among others. Preferably, the oxidizing agents and the precipitating reagent are provided in prepackaged packets, tubes or bottles which contain the necessary chemicals in the appropriate amounts. Preferred embodiments of the containers for the reactants are illustrated in FIGS. 9–14.

For example, the test kit of the invention may be provided with packets of various constructions which keep the needed chemicals separate until used. In the embodiment of FIG. 9, the packets are combination barrier and outer material laminations wherein one packet contains the first oxidizing agent, another packet contains the precipitating agent and a third packet contains the second oxidizing agent. The dye can be contained in a packet or test swab formulation. The packets are opened when needed by tearing a corner off and pouring the contents into the container holding the liquid sample.

In the embodiment of FIG. 10, the packets are small vacuum formed containers which hold the chemicals and are sealed until use by a barrier foil adhered to the containers. The packets may be included in the test kit attached by perforations. As the chemicals are needed, the packets are separated at the perforations, a corner is torn off and the foil top is peeled away. This embodiment is similar to a single serve coffee cream container. FIG. 11 illustrates a similar embodiment wherein the chemical containers have a bottom tab which is broken off and the contents poured into the container holding the liquid sample to be tested.

In other embodiments illustrated in FIGS. 12–14, the chemicals are stored in tubes which can be sealed until use. These embodiments enable the use of nonbreakable tubes which contain breakable cartridges containing the reactants for the desired test, which is described in U.S. Pat. Nos. 5,039,618; 5,278,075; 5,330,917; and 5,364,792 and U.S. patent application Ser. No. 08/325,149.

For example, in one embodiment, a cardboard tube can be prepared containing a glass vial of precipitating reagent and a glass vial of a carrier metal. The tube is fitted with a plastic screen plug and a plastic or vinyl cap. When the precipitating reagent is needed, the glass vials are broken and the chemicals mixed and poured into the container with the liquid sample, with the screen keeping the broken glass particles inside the cardboard tube. This embodiment keeps the chemicals separate until use.

In a preferred embodiment, the dye is introduced onto the precipitate by an apparatus which comprises a cartridge, two compartments within said cartridge wherein one compartment contains a reagent that reacts with the substance and the other compartment contains an activating solution, and an absorbent ball or medicine dropper tip mounted at one end of the cartridge, wherein the reagent and activating solution are combined and mixed within the cartridge before the means for introducing a dye is used. Some of the reagents and activating solutions which can be used are listed in Table I.

The type of cartridges or bottles used to contain the chemistry is dependent on the nature of the particular chemicals used. Thus, if the chemicals are liquid, a dropper type bottle may be used. If the chemicals are powder or dry, a shaker type bottle may be used.

In a further embodiment, the chemicals may be stored directly in the container for holding the liquid sample or in a cap for the container, such as described in U.S. patent application Ser. No. 08/257,430, the subject matter of which is hereby incorporated herein by reference. The chemicals may be provided in foil sealed vessels, in tablet form, in capsules, or in breakable cartridges to be broken as needed.

Figure 8:
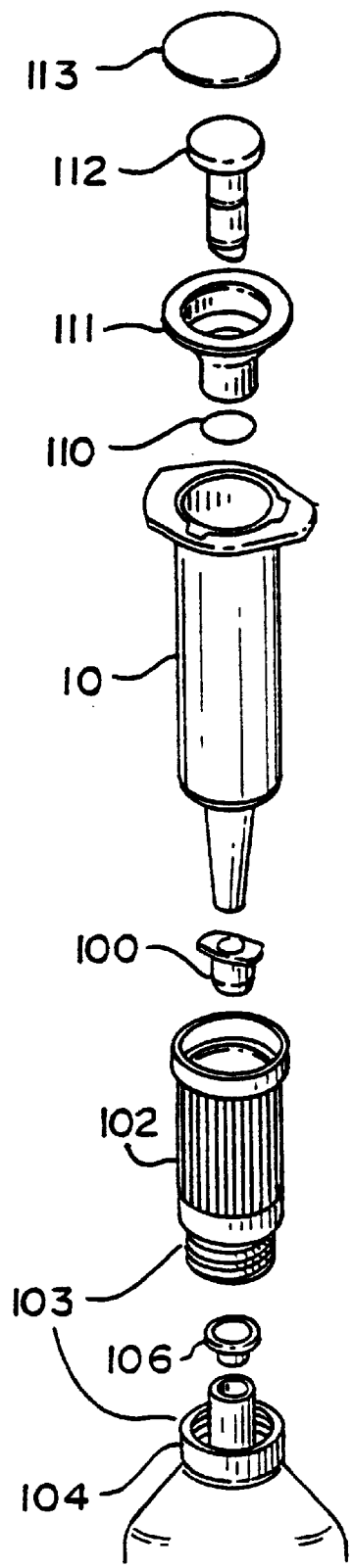
FIG. 8 is an exploded view of a preferred embodiment of the test apparatus of the present invention.

FIG. 8 illustrates an embodiment of a test apparatus according to the present invention having a 100 ml syringe 10, tip cap 100, filter holder 103 having a support or upper housing 102 and a lower housing 104, and a filter 106. Syringe 10 is provided with a foil seal at 110 which is placed between the syringe and outer reagent packet 111. Inner reagent packet 112, which may have a somewhat sharp lower edge, is then placed inside outer reagent packet 111 and covered by foil seal 113. The user can take the reagent packets out of the top of the syringe when ready to use the apparatus and place the liquid sample in the syringe. Then, the reagent packets are placed in the top of the syringe and pushed downward, breaking the seals and releasing the chemicals into the liquid sample. The sharp edge of the inner reagent packet, or other means, can be used to break the foil seals. Prior to carrying out the filtering procedure, the tip cap 100 will be removed from syringe 10, filter holder 103 is attached and a plunger (not shown) is introduced into the container.

FIGS. 15–18 illustrate additional embodiments for storing the chemicals inside the container for the liquid sample. The chemicals can be lifted out of the container prior to placing the liquid sample in the container or left inside, depending on the form of the chemicals. FIG. 15 shows tablets 90 containing the precipitating reagents which are placed in syringe 10 and foil sealed at 91. FIG. 16 shows gelatin capsules 92 containing the reagents and placed in the syringe covered by custom molded cap 93. The tablets or capsules are preferably dissolvable upon contact with the liquid sample.

Figures 17, 18:
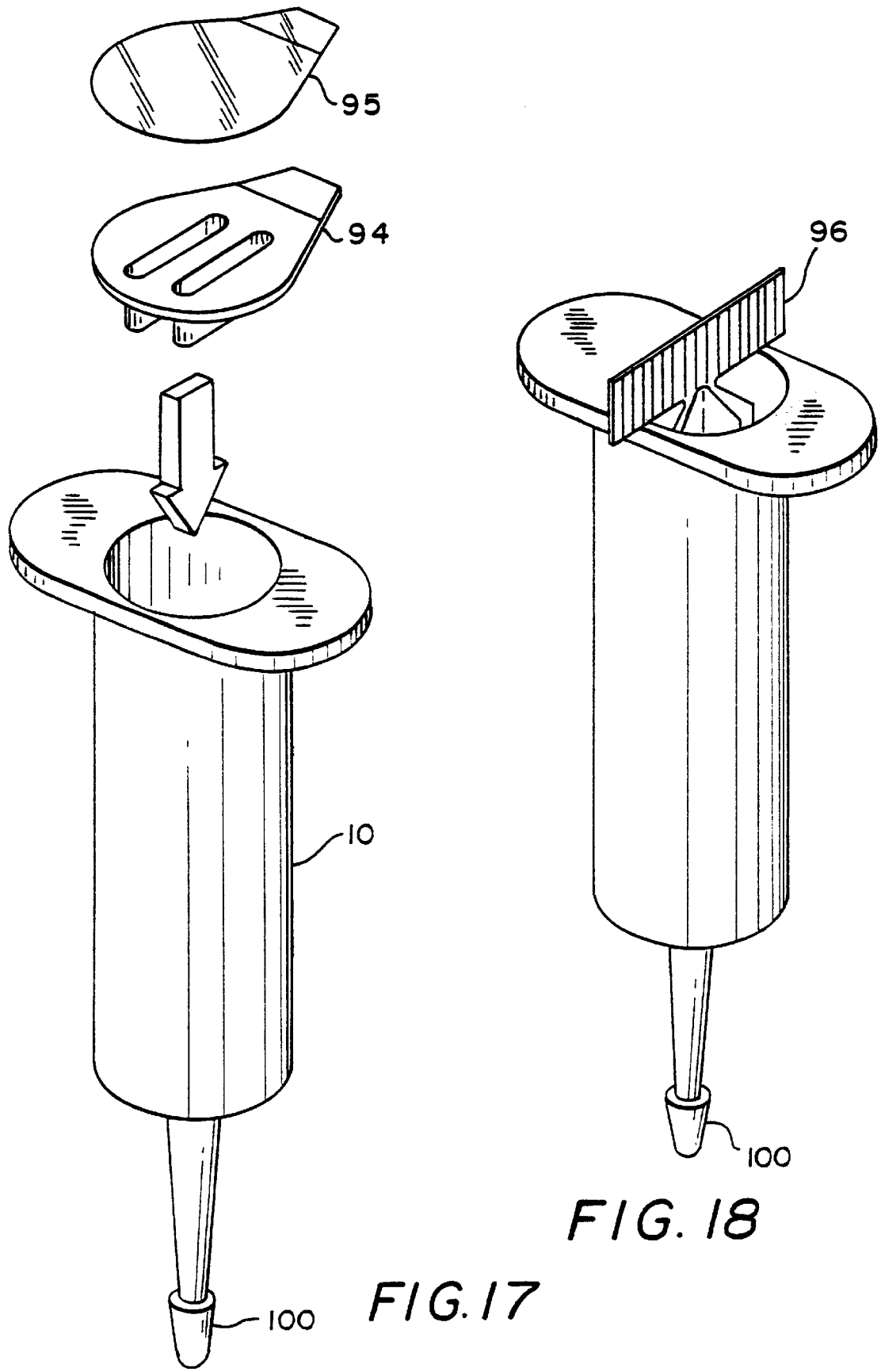

FIG. 17 illustrates a vacuum formed tray with separate compartments for the precipitating reagent and the carrier metal. The tray is protected by foil seal 95. FIG. 18 illustrates a twist open pack 96 for holding the reactants which fits into the barrel of the syringe.

FIGS. 19–21 illustrate embodiments of the test kit of the present invention utilizing squeeze tubes, similar to toothpaste tubes, or plunger designs for use with the container for the liquid sample. In FIG. 19, the squeeze tube 200 is filled with about 50 ml of water, a cap (not shown) is placed over the end of the tube and the tube is shaken to mix the water with the precipitating agent, buffer and carrier metal already in the tube at 204. After standing for about 10 minutes, the cap is changed to a filter top 202 with filter 205 and the tube is rolled up to expel the water and collect the precipitate. A releasing agent, such as hydrogen peroxide, is provided in a capsule 206, which will break as the tube is rolled or can be cracked manually. The releasing agent is allowed to react with the precipitate for as long as needed. A calorimetric test for the metal of interest can then be performed.

Alternatively, the reactants may be carried in the plunger of a syringe in breakable cartridges which can be crushed when needed. FIG. 20 illustrates a syringe plunger 300 with breakable cartridges 302, 304, and 306 which contain the pretreating agent, the precipitating reagent, and carrier, respectively. The bottom 308 of the plunger 300 includes a plurality of apertures 310, through which the precipitated sample may be introduced into the main body of the syringe (not shown), such as syringe 10 of FIG. 1. A cap 312 fits over the syringe bottom 308, and prevents the precipitated sample from leaving the plunger 300 until the cap 312 is removed.

FIG. 21 illustrates a syringe plunger 400 with an inner plunger 402 and breakable cartridges 404, 406, and 408 which contain the pretreating agent, the precipitating reagent, and the releasing agent, respectively. The bottom 410 of the plunger 400 includes a plurality of apertures 412, through which the precipitated sample may be introduced into the main body of the syringe (not shown), such as syringe 10 of FIG. 1. A cap 414 fits over the syringe bottom 410, and prevents the precipitated sample from leaving the plunger 400 until the cap 414 is removed.

In the FIG. 21 embodiment, the outer plunger 400 is squeezed as needed to break inner cartridges 404 and 406 for reaction. The inner plunger 402 is used to break the peroxide cartridge 408.

Any of the above embodiments may be provided such that the apparatus is reusable by providing the test kit with multiple packets or capsules of reactants and multiple filters or filter units for multiple samples.

The following examples illustrate the invention. It is understood, however, that these examples are not to be interpreted as limiting the scope of the invention. All percentages in the examples, and elsewhere in the specification, are by weight unless otherwise specified.

Figure 22:
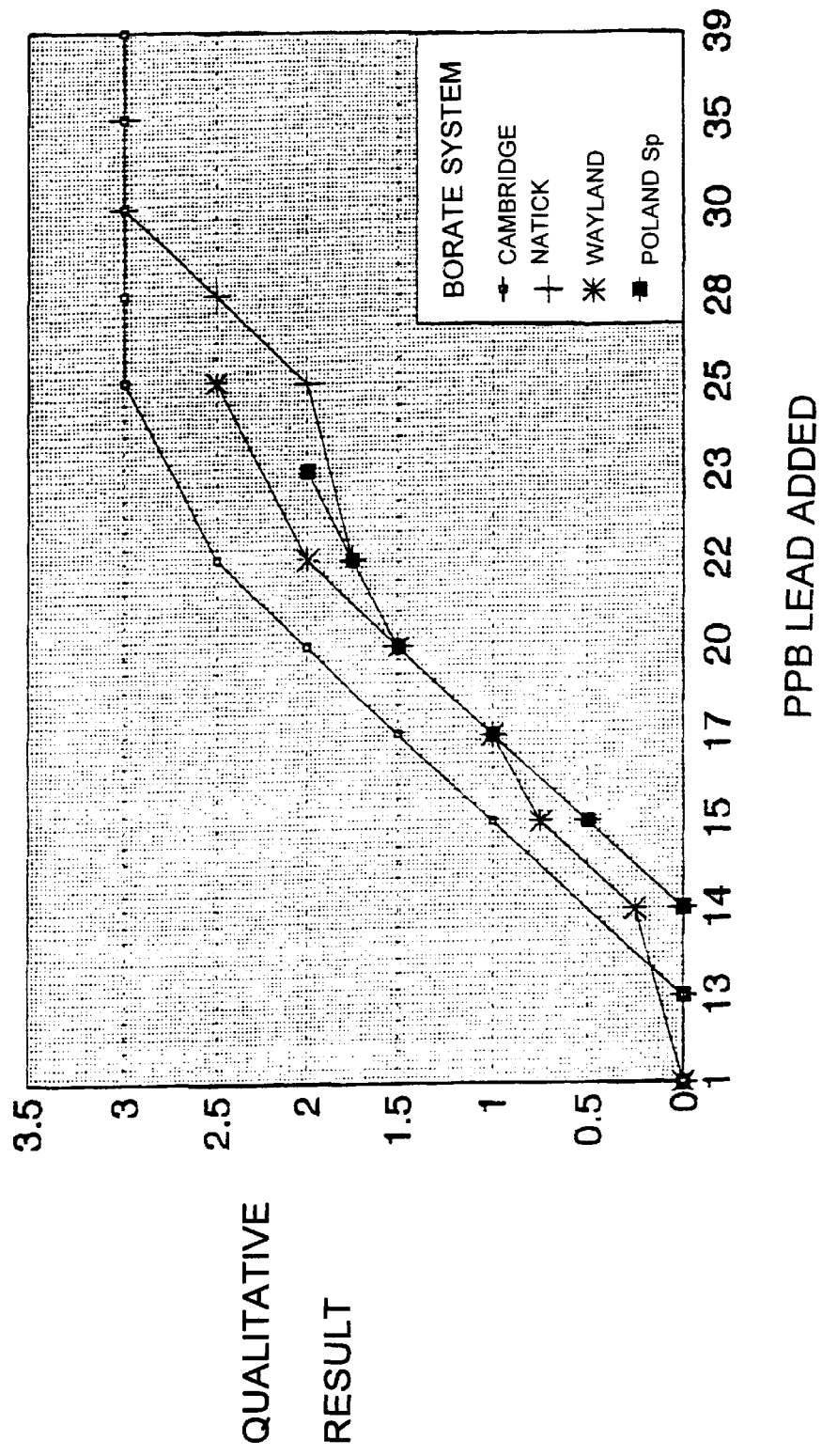
FIGS. 22 and 23 are charts illustrating the sensitivity of tests according to the present invention.

FIG. 22 illustrates a number of tests using the present invention. Specifically, 100 ml samples of water from four different sources were treated with a predetermined quantity of lead so that the treated samples had between 0 and 35 ppb of lead in them. The samples were then pretreated with CLOROX®, as taught above, and combined with 0.45 mg of zinc acetate (as a carrier).

A borate tablet containing 80 mg of borate was then added to each sample to precipitate the lead. After precipitating the lead, the samples were pushed through a filter using the apparatus disclosed in this application. The filters were then tested for lead precipitate using the solution from a LEAD-CHECK® lead test swab. No releasing agents were used on the precipitate prior to testing the precipitate for lead.

According to FIG. 22, the tests were able to detect lead in the samples at levels ranging from 14 ppb and greater. A "Qualitative Result" greater than 0 in the abscissa of the chart in FIG. 22 merely indicates a pink or red color appeared in the presence of the LEADCHECK® solution. Such a result is a positive indication for the presence of lead.

Figure 23:
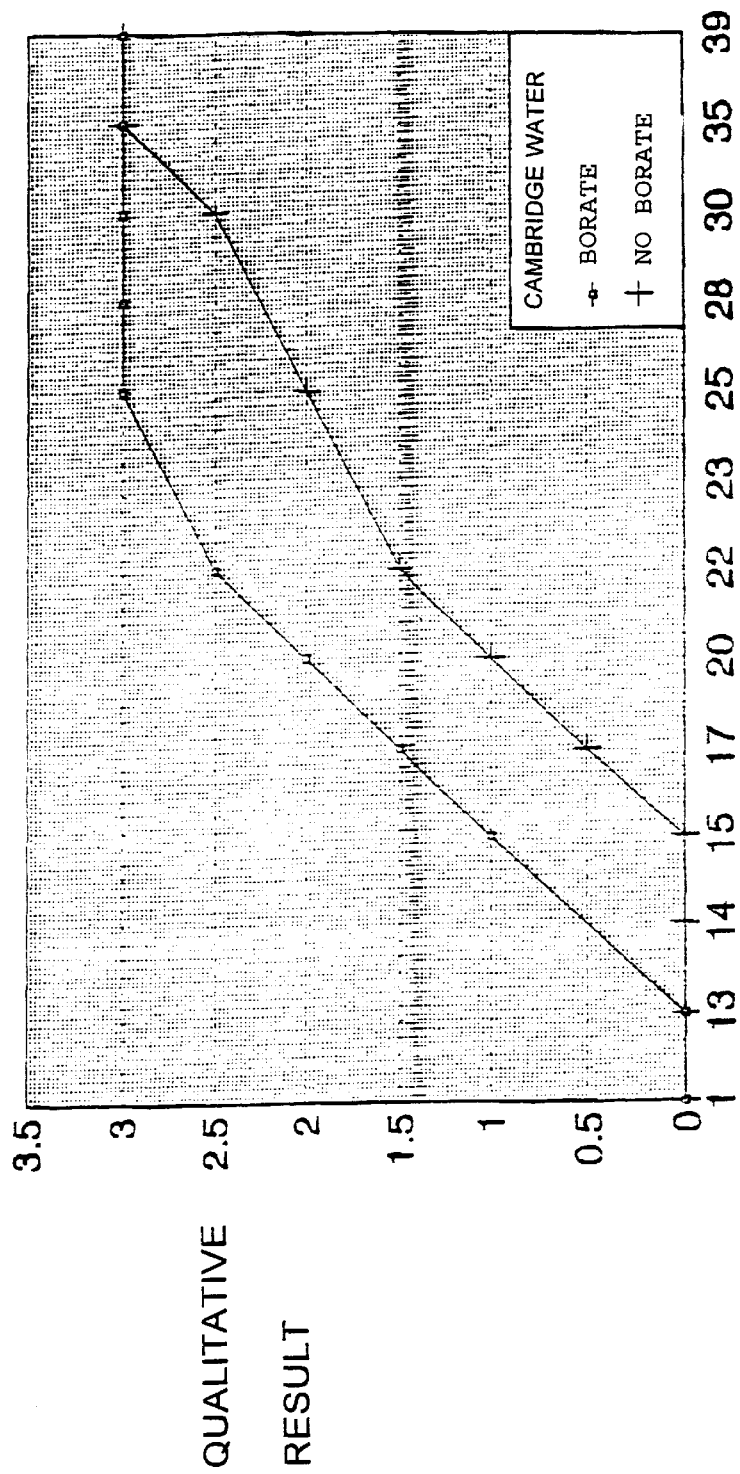

According to FIG. 23, the line in the chart identified by "Borate" reflects the same test results as the line in FIG. 22 that is marked "Cambridge".

In yet another embodiment of the present invention, it was surprisingly discovered that if lead is present in a liquid sample, such as water, a small, yet detectable quantity of lead adheres to, or is adsorbed by, a filter through which the sample is pushed. Specifically, nonspecific adhering of lead onto the filter was detected with glass fiber filters, such as Gelman Type A/E glass fiber (pore size: 1 micron), PFG3 filter (millipore 1.2 micron), PFG2 filter (Millipore 1.0 micron) or PFG5 filter (Millipore 0.7 micron). In addition, detectable quantities of lead were also found when a hydrophilic polysulfone membrane filter was used.

It has also been discovered that the effects of the filter can be enhanced by placing small glass beads on the filter prior to pushing the sample through the filter. For example, glass beads having a mesh size of 120–200 with a mean pore diameter of 115 Å have been used.

According to this embodiment of the present invention, a liquid sample is pushed through a filter using any of the apparatus disclosed above. A 100 ml sample was pushed through a glass filter having a diameter of 7 mm. The filter was then tested by applying 100 to 300 µl of the solution from a LEADCHECK® test swab, which includes sodium rhodizonate. See U.S. Pat. Nos. 5,039,618; 5,278,075; 5,330,917; and 5,364,792 and U.S. patent application Ser. No. 08/325,149.

The filters turned pink if lead was present in the sample. The results of these tests are illustrated in FIG. 23 by the line marked "No Borate". FIG. 23 illustrates that samples having lead concentrations as low as 17 ppb were detected as having lead without using any precipitator.

The diameter of the filter should not be too large since a purpose of the filtering procedure is to concentrate the metal in a small area. The sensitivity of the test may be reduced if the metal is spread out too much on the filter. Generally, the filter should be from about 7 mm to about 17 mm in diameter for a 100 ml sample. Preferably, the filter is from about 10 mm to about 15 mm in diameter. The preferred diameter of the filter is proportional to the amount of sample pushed through the filter.

Thus, for a 100 ml sample, the sample to filter area ration will be approximately $100/227$ ml/mm$^2$ for a 17 mm diameter filter, $100/79$ ml/mm$^2$ for a 10 mm diameter filter, and $100/38$ ml/mm$^2$ for a 7 mm diameter filter.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for detecting lead in a liquid sample comprising:

mixing the liquid sample with a first reagent that comprises borate and causes the lead to precipitate;

filtering the precipitate from the liquid sample; and testing the precipitate for lead by contacting the precipitate with a second reagent that forms a calorimetric reaction when exposed to lead.

2. The method of claim 1, further comprising pretreating the liquid sample with an oxidizing agent prior to mixing the liquid sample with the first reagent.

3. The method of claim 2, wherein the oxidizing agent comprises sodium hypochlorite.

4. The method of claim 1, wherein the first reagent further comprises a buffer and a carrier metal that has less affinity for the second reagent than lead.

5. The method of claim 4, wherein the carrier metal comprises zinc acetate.

6. The method of claim 1, wherein the second reagent comprises sodium rhodizonate.

7. A method for detecting a metal selected from the group consisting of lead, cadmium, bismuth, mercury, cobalt, iron, and copper in a liquid sample comprising:

mixing the liquid sample with borate to cause the metal to precipitate;

filtering the precipitate from the liquid sample; and testing the precipitate for the metal by contacting the precipitate with a reagent that forms a calorimetric reaction when exposed to the metal.

8. The method of claim 7, further comprising pretreating the liquid sample with an oxidizing agent prior to mixing the liquid sample with the borate.

9. The method of claim 8, wherein the oxidizing agent comprises sodium hypochlorite.

10. The method of claim 7, wherein the sample is also mixed with a buffer and a carrier metal that has less affinity for the reagent than the metal to be detected.

11. The method of claim 10, wherein the carrier metal comprises zinc acetate.

12. The method of claim 7, wherein the metal is lead and the reagent comprises sodium rhodizonate.

\* \* \* \* \*